United States Patent [19]

Gerlier et al.

[11] 4,201,478
[45] May 6, 1980

[54] PHOTOMETER WITH AUTOMATIC TEST SAMPLE SELECTION, SCANNING AND ANALYSIS SYSTEM

[75] Inventors: Jean-Pierre Gerlier, Saint-Maur-les-Fosses; Jacques Augier, Paris, both of France

[73] Assignee: Institut Pasteur, Paris, France

[21] Appl. No.: 843,209

[22] Filed: Oct. 18, 1977

[30] Foreign Application Priority Data

Oct. 19, 1976 [FR] France ................. 76 31423

[51] Int. Cl.$^2$ ............................................. G01N 21/22
[52] U.S. Cl. .................................... 356/440; 356/244; 356/409; 422/65
[58] Field of Search .................. 356/96, 97, 201, 244, 356/246, 180, 184, 440, 409; 422/63, 65

[56] References Cited

U.S. PATENT DOCUMENTS

| | | | |
|---|---|---|---|
| 3,829,221 | 8/1974 | de Mendez et al. ................. | 356/201 |
| 3,897,216 | 7/1975 | Jones ..................................... | 356/246 |
| 3,985,507 | 10/1976 | Litz et al. ............................. | 356/244 |

*Primary Examiner*—Vincent P. McGraw
*Attorney, Agent, or Firm*—James & Franklin

[57] ABSTRACT

The photometer for automatic sample analysis comprises an optical bench emitting a measuring lightbeam, a series of transparent cells containing the samples for analysis and for sucessive presentation in the beam and result recording and processing means. A set of rectilinear presentation means each supporting a juxtaposed row of cells is arranged in parallel side by side in a magazine. Means for selecting and extracting each presentation means successively from the set of the latter are provided. A movable carriage supports the optical bench with means for moving said carriage at reading speed parallel to the row of cells selected such that the measuring beam of the bench sucessively traverses each cell of said row.

34 Claims, 6 Drawing Figures

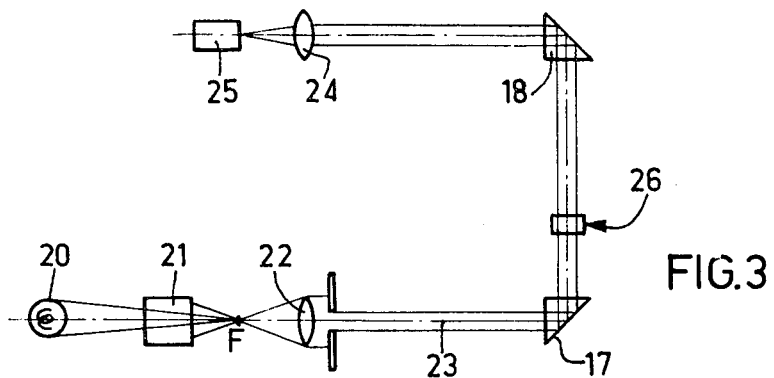
FIG.3
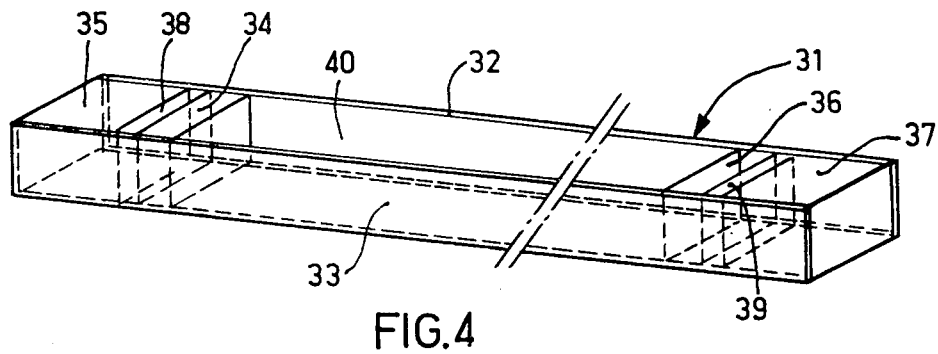
FIG.4
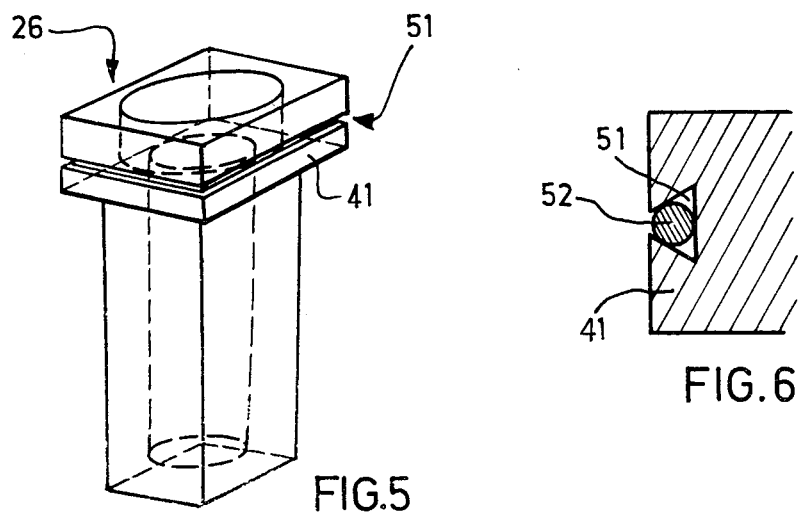
FIG.5
FIG.6

PHOTOMETER WITH AUTOMATIC TEST SAMPLE SELECTION, SCANNING AND ANALYSIS SYSTEM

BACKGROUND OF THE INVENTION

1. Field of the Invention

The present invention relates to an automatic photometer for sample analysis.

The invention applies more particularly to automatic comparative measurements of the optical densities of solutions contained in a series of transparent cells.

The problem consists of analysing, by comparison with a test cell, chemical, biochemical or bacteriological reactions carried out in separate cells; given that the cells containing the samples are analyzed comparatively, the measurements must be done rapidly to obviate the influence of the time factor and, of course, the solutions must be protected from soils and contaminations.

2. Description of the Prior Art

Present known apparatus is of two types; on the one hand that including a fixed optical bench producing a measuring lightbeam into which the cells containing the samples are brought one after the other and, on the other hand, that including a fixed optical bench and an analysis cell likewise fixed situated in the measuring beam, each sample of solution being sent successively into the cell by pumping.

The first type of apparatus has the drawback of requiring complex mechanism due to the fact that each cell must be transported in space along three dimensions; as for equipment of the second type, it has the serious drawback of mixing the solutions in the analysis cell and of thus soiling the samples, which is troublesome both from the biological point of view and from the physical measurement point of view.

Lastly, the two types of equipment are slow and require a large number of manipulations which multiply the risks of contamination.

It is therefore an object of the invention to provide a photometer capable of carrying out measurements automatically, with rapidity and under optimal conditions of protection against soils, the apparatus forming furthermore a sterilizable assembly.

GENERAL DESCRIPTION OF THE INVENTION

The photometer for the automatic analysis of samples according to the invention comprises an optical bench emitting a measuring lightbeam, a series of transparent cells containing the samples to be analysed arranged to be presented successively in the beam and recording and processing means for the results, said photometer including, in addition, rectilinear presentation means each supporting a row of juxtaposed cells, a storage magazine receiving the presentation means arranged parallel side by side, means for selecting and extracting successively each presentation means from the set of the latter, a movable carriage supporting the optical bench and means for moving said carriage at the reading speed parallel to the selected row of cells so that the measuring beam passes successively through each cell of said row.

BRIEF DESCRIPTION OF THE DRAWINGS

The invention will now be described in more detail, with reference to a particular embodiment given purely by way of non-limiting example and shown in the accompanying drawings, in which:

FIG. 3 shows a diagrammatic view of the optical bench of the photometer according to the invention.

FIG. 4 shows an embodiment of a presentation means used in the photometer according to the invention.

FIG. 5 shows a perspective view of a cell for holding a sample, for a photometer according to the invention.

FIG. 6 shows a cross-section of the rim of the cell of the embodiment shown in FIG. 4.

DESCRIPTION OF A PREFERRED EMBODIMENT

Figure 1:
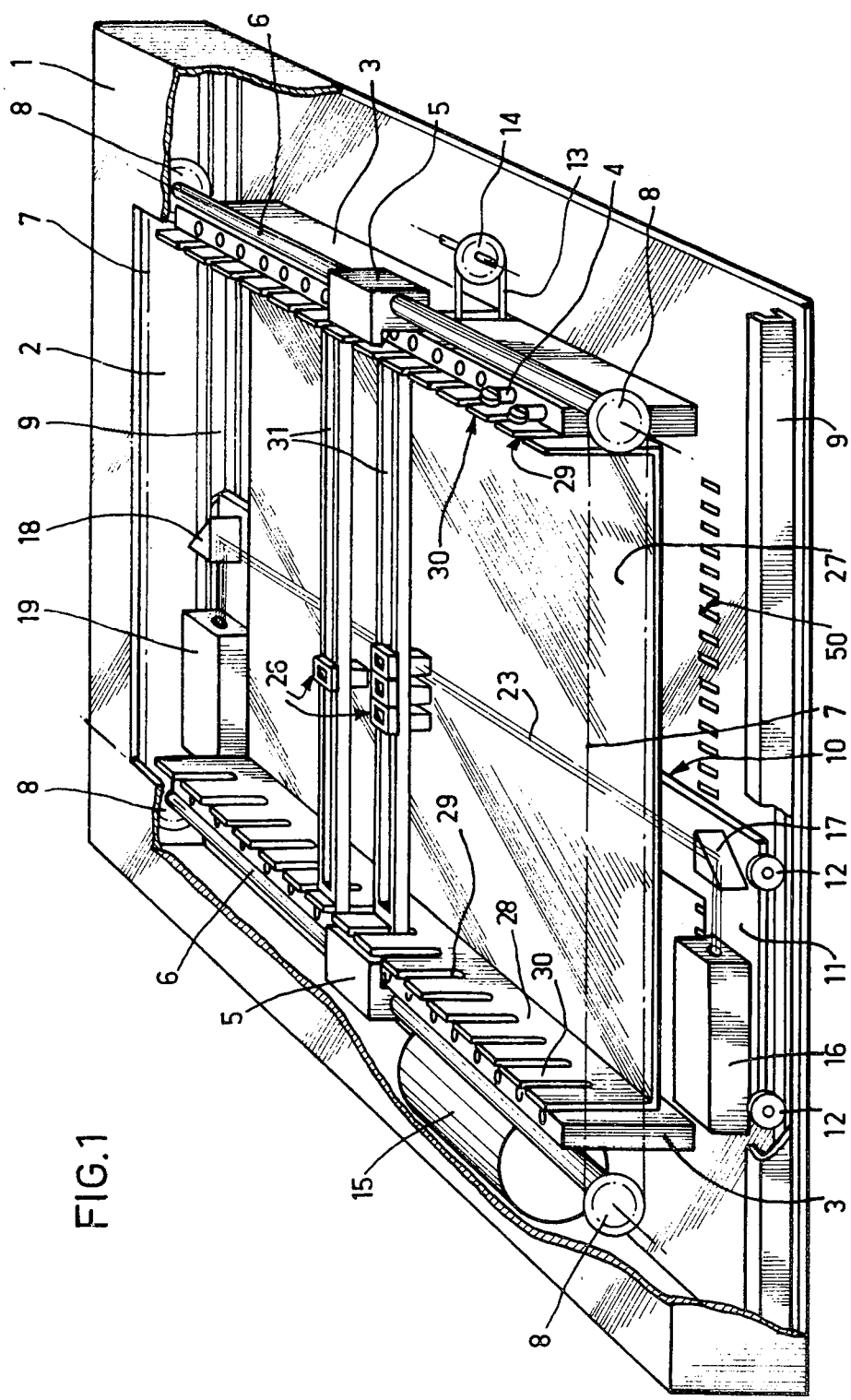
FIG. 1 shows a torn-away view of an embodiment of a photometer according to the invention.

As shown in FIG. 1, this embodiment of the photometer according to the invention comprised a parallelepipedic housing 1 of sheet metal of flat shape, provided with a rectangular opening 2 at the upper part, said opening being closed in sealed manner by a cover (not shown).

Along two opposite edges of the opening 2 and inside the housing 1 are arranged face to face two ramps 3 with vertical pushers 4 actuated by two cams 5 which move together above said pushers parallel to said ramps 3, the simultaneous rectilinear displacements of said cams being produced by the concordant rotation of two screws screwed respectively through the body of each of the cams and forming two screw-nut systems. The screws 6 are mutually servo-coupled by chains 7 engaging identical pinions 8 mounted at the end of said screws, so that the latter rotate at the same speed and simultaneously drive the cams 5 which are moved while remaining constantly face to face on the same transverse line perpendicular to the parallel ramps 3.

Parallel to the two other opposite edges of the opening 2, along the lateral walls of the housing 1 perpendicular to the ramps 3, are fixed two slides 9 in the form of U-sectional elements which serve to guide the movement of a movable carriage 10 bearing the optical bench of the photometer according to the invention. The carriage 10 is composed of a horse-shoe plate 11 mounted on rollers 12, said carriage being driven in translation by a traction chain 13 engaging with two aligned sprocket wheels 14 situated on each side of the housing behind the pushing ramps.

A reducing gear drive unit 15 actuates with rapid backward return the conjugated movements of the screws 6 driving the cams 5 and the moveable carriage 10 displacing the optical bench perpendicularly to the movement of the latter.

The movable optical bench is composed essentially of an emitter 16, a first prism 17, a second prism 18 and a collector 19, the emitter 16 and the prism 17 being carried by one arm of the horse-shoe plate 11 while the prism 18 and the collector 19 are born by the opposite arm of said plate, so that the two prisms 17 and 18 situated face to face move parallel from one ramp 3 to the other respectively at two ends of the latter.

The emitter 16 includes (FIG. 3) a light source 20 constituted by a microscopy lamp with point filament, and an objective 21 giving a quasi-point image of said filament at the focus F of a collecting lens 22; the parallel beam 23 thus created is sent to the prism 17 which deflects it a first time to send it back parallel to the pusher ramps 3 onto the second prism 18 situated on the other side of the housing which deflects it a second time in the direction of the collector 19 which includes a condenser 24 and a detector 25, the condenser concentrating the beam onto the lens of a photo-transistor constituting said detector, the elements of the optical bench being of course adjustable, notably in position.

Due to the fact of the respective positions of the two prisms 17 and 18, the part of the parallel beam 23 going from one to the other sweeps the space comprised between the two parallel ramps 3 when the carriage 10 and the associated optical bench move along the slide 9. In this space is arranged a storage magazine for the cells 26 for receiving the samples to be analysed, said magazaine being in the form of a tray 27 including vertical slots 29 distributed regularly along the latter and defining as many vertical guide tongues 30.

To each tongue 30 cut out in one lateral wall 28 of the magazine corresponds another tongue cut out face to face in the opposite wall and each pair of tongues 30 serves for the vertical guidance of a presentation means 31 whose ends are engaged on the latter, the tray assembly 27 being covered with presentation means arranged parallel side by side. Each presentation means supports a row of juxtaposed analysis cells 26 suspended above the tray 27 in the space swept by measuring beam 23.

As shown in FIG. 4, each presentation means 31 has the shape of a rule whose central portion has been hollowed out to leave only two parallel lateral walls 32 and 33 joined at the end by two pairs of cross-pieces 34–35 and 36–37, the cross-pieces 34 and 36 being separated respectively from the cross-pieces 35 and 37 so as to form two guide slots 38 and 39 at the two ends of the presentation means. The walls 32 and 33 define between them a groove 40 for receiving the analysis cell 26, which includes a rim 41 serving to suspend them on said walls, one beside the other. Each presentation means 31 provided with its rows of cells 26 is placed in the storage magazine, so that two corresponding tongues 30 arranged face to face are engaged in the guide slots 38,39 of said presentation means which is thus retained longitudinally and transversely, but can be displaced vertically by sliding along its guide tongues 30.

Figure 2:
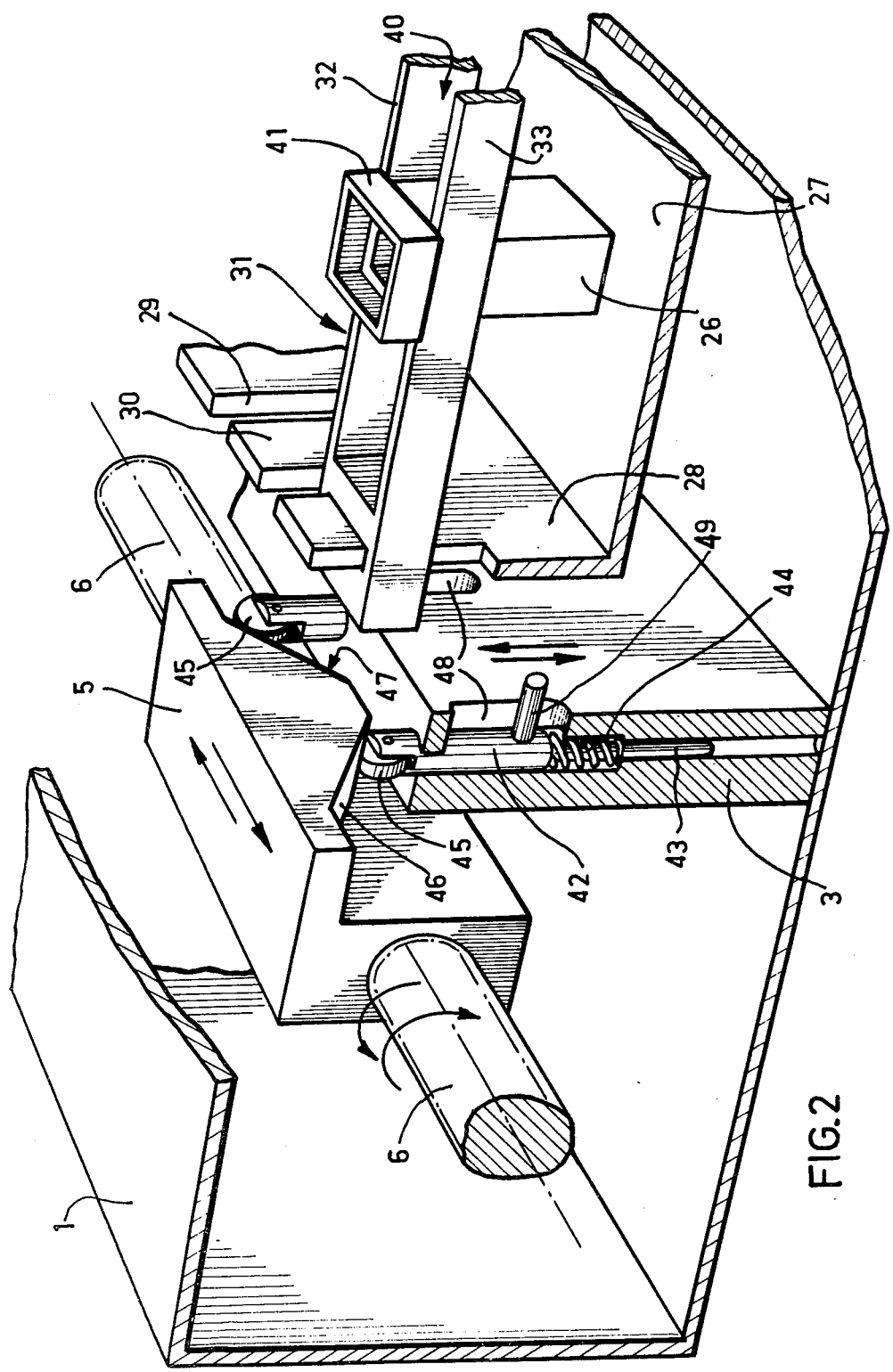
FIG. 2 shows an enlarged perspective view of the means for the selection of the presentation means, of the embodiment of FIG. 1.

As can be distinguished, even on the enlarged view of FIG. 2, the lateral push ramps 3 include a series of vertical bores equal in number to the number of tongues 30 of the storage magazine and distributed regularly in which are slidably mounted pushers 4 whose cylindrical bodies 42 rest on helicoidal springs 44 wound around cylindrical guide stems 43 extending from said bodies downward; at their upper end, said bodies terminate in a fork in which a roller 45 is rotatively mounted for rolling along the inclined ramps 46 and 47 provided on the cams 5, said ramps being symmetrical in respect to the vertical and forming between them an angle of about 45 degrees. Vertical ports 48 are formed in the surface of the bores of the ramps 3 in which the bodies 42 of the pushers slide, said ports serving to guide support fingers 49 vertically, fixed for example by screwing perpendicularly to the body 42 of the pushers 4. The support fingers 49 extend beyond the walls of the ramps 3 situated opposite and are distributed along the latter so that each finger 49 occurs facing a tongue 30 when the storage magazine is placed in the photometer, the presentation means 31 resting by means of their cross-pieces 35 and 37 on two aligned fingers 49, directed on toward the other and projecting on the facing surfaces of the two ramps 3.

On the bottom of the housing 1 is provided a graduated rule 50 for an electronic detector (not shown) mounted under the plate 11 of the optical bench, each graduation corresponding to an alignment of cells 26 perpendicular to the presentation means 31.

FIG. 5 shows a cell of transparent plastics material including at the upper part a rim 41 provided at its periphery with a groove 51 of dove-tail cross-section (FIG. 6), said groove serving to join together a row of cells by means of a wire 52, for example of nylon, of diameter slightly greater than the width of the entry slots of the grooves 51, the wire being force-fitted and caught in the latter.

Lastly, the photometer according to the invention includes a logic unit which governs all the functions of the system as well as an logarithmic amplifier and an external calculator with output printer for processing the measurements.

The photometer described above operates in the following manner:

The samples to be analyzed being each placed in a separate cell 26, said cells are suspended side by side on the presentation means 31, thirty per presentation means, fifteen of them are placed in the storage magazine 27, one behind the other, with their ends engaged on the tongeus 30 so as to be able to slide vertically. At the beginning of each row of cells born by one presentation means is placed a test cell serving as a reference for the measurements carried out on the samples of the row.

The magazine 27 is then closed in sealed manner by a cover (not shown) then deposited in the housing through the opening 2, so each presentation means 31 is supported by the two ends by two associated support fingers 49, the support fingers holding the presentation means in upper position as shown in FIG. 2. The measuring cycle is triggered by a push-button.

All the operations of the system are then governed automatically by the logic unit.

The cams 5 driven by the rotation of the screws 6 commence their advance and their ramps 47 push back downward the first two pushers 4 whose descent drives that of the first presentation means 31 and of its row of cells which then passes below the other cells whose presentation means are still in upper position.

The movable carriage 10 supporting the optical bench then moves from one end of the row of cells to the other end, the measuring lightbeam 23 thus sweeping the row of cells lowered into its path registering each cell successively by means of the graduations of the scale 50.

The measuring beam analyses each sample at a distance, the intensity of the beam which has passed through a cell being measured and processed numerically so as to obtain the optical density (O.D.) of each solution, as well as the O.D. ratios; the signal supplied by the detector is amplified, processed by the logarithmic amplifier, converted into numeric form and then processed by an external computer with an output printer. If $I_o$ is the intensity of the incident beam, $I_1$ the intensity of the beam emerging from the compression cell and $I_2, I_3, \ldots I_n$ the intensities of the beams which have passed respectively through the $2^{nd}, 3^{rd} \ldots n^{th}$ cell, then the optical densities will be:

$$OD_2 = K \log I_1/I_2; \; OD_2 = K \log I_1/I_3; \; OD_n = K \log I_1/I_n$$

For a measurement of OD, it is therefore necessary to have a calibrated solution or an absorption standard such that $OD_2 = 1$.

It is observed that, whatever the intensity of the incident beam $I_o$, the result remains correct.

When the measuring lightbeam has passed successively through the n lowered cells of a row with read off on the graduation of the rule 50 provided on the bottom of the housing 1, the carriage 10 and the optical bench effect a rapid back return to the initial starting position; the cams 5 then advance by a notch, thus enabling the first presentation means to re-ascend under the action of the compressed return springs 44 and they oblige the second presentation means to be lowered and to present its row of cells below the other cells, at the level of the path of the measuring lightbeam.

The scanning of the new rows is carried out in the same manner and the cycle recommences until all the rows of cell of the magazine 27 have been scanned.

Given that, for each row of cells, the measurements are always reduced to that carried out on the test cell placed at the head of the row, whatever the intensity of the incident beam, the comparative measurements are always valid.

With the photometer according to the invention, the time necessary for the measurements can be reduced in considerable proportions and these measurements are carried out automatically without any manual intervention; moreover, the magazine is sterilizable. All the operations, including those of the introduction or removal of the magazine in the photometer and the reading of the cell, are done with the cover closed.

The magazine is thus semi-sealed and possible soils cannot contaminate the photometric part.

The magazine is only opened during the operation of the inoculation and for the emptying of the cells after sterilization.

Of course, the scope of the invention is not limited to the single embodiment described above by way of non-limiting example, but it covers also any modification only differing in details.

Thus the carriage supporting the optical bench can be rectilinear or "L" shaped, or of any other suitable shape.

We claim:

1. Photometer for the automatic analysis of samples comprising
   (A) an optical bench emitting a measuring lightbeam,
   (B) a series of transparent cells containing the samples for analysis and for successive presentation in the beam,
   (C) result recording and processing means,
   (D) a set of rectilinear presentation means each supporting a juxtaposed row of said cells,
   (E) a magazine receiving said presentation means arranged in parallel side by side,
   (F) means for selecting and extracting each of said presentation means successively from the set of the latter,
   (G) a movable carriage supporting said optical bench, and
   (H) means for moving said carriage at reading speed parallel to the row of cells selected such that the measuring beam of said bench successively traverses each cell of said selected row;
   said magazine comprising a plate in the form of a tray and a cover undissociable from said tray during the measuring operations, said tray being provided laterally with two channelled opposite walls of which the channels define vertical guide tongues along which said presentation means can slide.

2. Photometer of claim 1, wherein each of said rows of cells is linear.

3. Photometer of claim 1, wherein said means for selecting and extracting said presentation means selects and extracts each of said presentation means successively from the set of the latter while simultaneously returning to a non-extracted disposition the presentation means immediately previously selected.

4. Photometer of claim 1, wherein said means for selecting and extracting said presentation means comprise two rows of vertical pushers aligned opposite each other and two simultaneously movable cams moving to push them above said pushers, said pushers being provided with horizontal lateral fingers for supporting said presentation means and their cells.

5. Photometer for the automatic analysis of samples comprising
   (A) an optical bench emitting a measuring lightbeam,
   (B) a series of transparent cells containing the samples for analysis and for successive presentation in the beam,
   (C) result recording and processing means,
   (D) a set of rectilinear presentation means each supporting a juxtaposed row of said cells,
   (E) a magazine receiving said presentation means arranged in parallel side by side,
   (F) means for selecting and extracting each of said presentation means successively from the set of the latter,
   (G) a movable carriage supporting said optical bench, and
   (H) means for moving said carriage at reading speed parallel to the row of cells selected such that the measuring beam of said bench successively traverses each cell of said selected row;
   said magazine comprising a plate in the form of a tray, said tray being provided laterally with two channelled opposite walls of which the channels define vertical guide tongues along which said presentation means can slide.

6. Photometer according to claim 5, wherein said presentation means are hollow rules comprising at the two ends guide slots provided for engagement on said guide tongues of said magazine.

7. Photometer according to claim 5, wherein said movable carriage supporting said optical bench is of horseshoe shape.

8. Photometer of claim 5, wherein each of said rows of cells is linear.

9. Photometer of claim 5, wherein said means for selecting and extracting said presentation means selects and extracts each of said presentation means successively from the set of the latter while simultaneously returning to a non-extracted disposition the presentation means immediately previously selected.

10. Photometer of claim 5, wherein said means for selecting and extracting said presentation means comprise two rows of vertical pushers aligned opposite each other and two simultaneously movable cams moving to push them above said pushers, said pushers being provided with horizontal lateral fingers for supporting said presentation means and their cells.

11. Photometer for the automatic analysis of samples comprising (A) an optical bench emitting a measuring lightbeam,
(B) a series of transparent cells containing the samples for analysis and for successive presentation in the beam,
(C) result recording and processing means,
(D) a set of rectilinear presentation means each supporting a juxtaposed row of said cells,
(E) a magazine receiving said presentation means arranged in parallel side by side,
(F) means for selecting and extracting each of said presentation means successively from the set of the latter,
(G) a movable carriage supporting said optical bench, and
(H) means for moving said carriage at reading speed parallel to the row of cells selected such that the measuring beam of said bench successively traverses each cell of said selected row;
said means for selecting and extracting each of said presentation means comprising two rows of vertical pushers aligned opposite each other and two simultaneously movable cams moving to push them above said pushers, said pushers being provided with horizontal lateral fingers for supporting said presentation means and their cells.

12. Photometer according to claim 11, wherein said two movable cams are driven by two screws servocoupled in rotation.

13. Photometer according to claim 11, wherein the movable carriage supporting the optical bench is of horseshoe shape.

14. Photometer of claim 11 wherein said magazine comprises a plate in the form of a tray, said tray being provided laterally with two channelled opposite walls of which the channels define vertical guide tongues along which said presentation means can slide.

15. Photometer of claim 11 wherein said magazine comprises a plate in the form of a tray, said tray being provided laterally with two channelled opposite walls of which the channels define vertical guide tongues along which said presentation means can slide, and wherein said presentation means are hollow rules comprising at the two ends guide slots provided for engagement on said guide tongues of said magazine.

16. Photometer of claim 11 wherein each of said rows of cells is linear.

17. Photometer of claim 11 wherein said means for selecting and extracting said presentation means selects and extracts each of said presentation means successively from the set of the latter while simultaneously returning to a non-extracted disposition the presentation means immediately previously selected.

18. Photometer for the automatic analysis of samples comprising
(A) an optical bench emitting a measuring lightbeam,
(B) a series of transparent cells containing the samples for analysis and for successive presentation in the beam,
(C) result recording and processing means,
(D) a set of rectilinear presentation means each supporting a juxtaposed row of said cells,
(E) a magazine receiving said presentation means arranged in parallel side by side,
(F) means for selecting and extracting each of said presentation means successively from the set of the latter while simultaneously returning to a non-extracted disposition the presentation means immediately previously selected and extracted,
(G) a movable carriage supporting said optical bench, and
(H) means for moving said carriage at reading speed parallel to the row of cells selected such that the measuring beam of said bench successively traverses each cell of said selected row.

19. Photometer of claim 18 wherein said means for selecting and extracting said presentation means comprise two rows of vertical pushers aligned opposite each other and two simultaneously movable cams moving to push them above said pushers, said pushers being provided with horizontal lateral fingers for supporting said presentation means and their cells.

20. Photometer of claim 18, wherein said magazine comprises a plate in the form of a tray, said tray being provided laterally with two channelled opposite walls of which the channels define vertical guide tongues along which said presentation means can slide.

21. Photometer of claim 18, wherein said magazine comprises a plate in the form of a tray, said tray being provided laterally with two channelled opposite walls of which the channels define vertical guide tongues along which said presentation means can slide, and wherein said presentation means are hollow rules comprising at the two ends guide slots provided for engagement on said guide tongues of said magazine.

22. Photometer of claim 18, wherein each of said rows of cells is linear.

23. Photometer for the automatic analysis of samples comprising
(A) an optical bench emitting a measuring lightbeam,
(B) a series of transparent cells containing the samples for analysis and for successive presentation in the beam,
(C) result recording and processing means,
(D) a set of rectilinear presentation means each supporting a juxtaposed linear row of said cells,
(E) a magazine receiving said presentation means arranged in parallel side by side,
(F) means for selecting and extracting each of said presentation means successively from the set of the latter,
(G) a movable carriage supporting said optical bench, and
(H) means for moving said carriage at reading speed parallel to the row of cells selected such that the measuring beam of said bench successively traverses each cell of said selected row.

24. Photometer according to claim 23, wherein said movable carriage supporting said optical bench is of horseshoe shape.

25. Photometer of claim 23, wherein said magazine comprises a plate in the form of a tray, said tray being provided laterally with two channelled opposite walls of which the channels define vertical guide tongues along which said presentation means can slide.

26. Photometer of claim 23, wherein said magazine comprises a plate in the form of a tray, said tray being provided laterally with two channelled opposite walls of which the channels define vertical guide tongues along which said presentation means can slide, and wherein said presentation means are hollow rules comprising at the two ends guide slots provided for engagement on said guide tongues of said magazine.

27. Photometer of claim 23, wherein said means for selecting and extracting said presentation means selects and extracts each of said presentation means successively from the set of the latter while simultaneously returning to a non-extracted disposition the presentation means immediately previously selected.

28. Photometer of claim 13, wherein said means for selecting and extracting said presentation means comprise two rows of vertical pushers aligned opposite each other and two simultaneously movable cams moving to push them above said pushers, said pushers being provided with horizontal lateral fingers for supporting said presentation means and their cells.

29. Photometer for the automatic analysis of samples comprising:

(A) a stationary magazine,
(B) a plurality of rectilinear presentation means arranged in parallel side by side in said magazine, each presentation means being movable vertically at its own location,
(C) a plurality of transparent cells containing the samples for analysis, said cells being juxtaposed in rows supported by said presentation means,
(D) means for selecting and moving vertically each presentation means out of the set of the latter,
(E) an optical bench emitting a measuring lightbeam vertically offset from the set of non-selected presentation means,
(F) a movable carriage supporting said optical bench,
(G) means for moving said carriage at reading speed parallel to said rows of cells such that the measuring beam of the bench successively traverses each cell of the selected presentation means, and
(H) result recording and processing means.

30. Photometer of claim 29, wherein said magazine comprises a plate in the form of a tray, said tray being provided laterally with two channelled opposite walls of which the channels define vertical guide tongues along which said presentation means can slide.

31. Photometer of claim 29, wherein said magazine comprises a plate in the form of a tray, said tray being provided laterally with two channelled opposite walls of which the channels define vertical guide tongues along which said presentation means can slide, and wherein said presentation means are hollow rules comprising at the two ends guide slots provided for engagement on said guide tongues of said magazine.

32. Photometer of claim 29, wherein each of said rows of cells is linear.

33. Photometer of claim 29, wherein said means for selecting and extracting said presentation means selects and extracts each of said presentation means successively from the set of the latter while simultaneously returning to a non-extracted disposition the presentation means immediately previously selected.

34. Photometer of claim 29, wherein said means for selecting and extracting said presentation means comprise two rows of vertical pushers aligned opposite each other and two simultaneously movable cams moving to push them above said pushers, said pushers being provided with horizontal lateral fingers for supporting said presentation means and their cells.

* * * * *